(12) United States Patent
Linssen et al.

(10) Patent No.: US 10,729,102 B2
(45) Date of Patent: Aug. 4, 2020

(54) CONTROLLABLE SCENT SAMPLE DISPENSER, AND ANIMAL TRAINING AND TESTING SYSTEM FOR DETECTING SCENTS

(71) Applicant: Fraunhofer-Gesellschaft zur Foerderung der angewandten Forschung e.V., Munich (DE)

(72) Inventors: Rene Linssen, Heerlen (NL); Martin Richter, Munich (DE); Sebastian Kibler, Munich (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 230 days.

(21) Appl. No.: 15/629,830

(22) Filed: Jun. 22, 2017

(65) Prior Publication Data

US 2017/0290294 A1   Oct. 12, 2017

Related U.S. Application Data

(60) Division of application No. 14/074,120, filed on Nov. 7, 2013, now abandoned, which is a continuation of
(Continued)

(51) Int. Cl.
*A01K 15/02* (2006.01)
*A61L 9/14* (2006.01)
*F41H 11/132* (2011.01)

(52) U.S. Cl.
CPC ............... *A01K 15/02* (2013.01); *A61L 9/14* (2013.01); *F41H 11/132* (2013.01);
(Continued)

(58) Field of Classification Search
CPC .... A01K 15/02; A01K 15/021; A01K 15/022; A61L 9/14; A61L 9/12; B05B 17/00;
(Continued)

(56) References Cited

U.S. PATENT DOCUMENTS 3,159,140 A * 12/1964 Miller .................. A01K 27/001
                                                                119/719
3,498,266 A *  3/1970 Miller .................. A01K 15/021
                                                                119/719
(Continued)

FOREIGN PATENT DOCUMENTS

DE        2610724 A1 *  9/1977  ............. A01K 15/02
DE        2649475 A1 *  5/1978  ............. A01K 15/02
(Continued)

OTHER PUBLICATIONS

Linssen et al., "Controllable Scent Sample Dispenser, and Animal Training and Testing System for Detecting Scents", U.S. Appl. No. 14/074,120, filed Nov. 7, 2013.

*Primary Examiner* — Kathleen I Alker
(74) *Attorney, Agent, or Firm* — Keating & Bennett, LLP

(57) ABSTRACT

A controllable scent sample dispenser has a microdosing device for outputting, during an activation state, a scent sample at a scent sample outlet to the environment, wherein the microdosing device is placeable adjacent to an animal's nose so that a distance between the outlet of the microdosing device and a nare or nostril of the animal's nose is within a predefined range, and a microdosing driver unit for adjusting a dosing rate of the scent sample output at the scent sample outlet by selectively activating the microdosing device.

5 Claims, 6 Drawing Sheets

Related U.S. Application Data application No. PCT/EP2011/057546, filed on May 10, 2011.

(52) U.S. Cl.
CPC .... *A61L 2209/111* (2013.01); *A61L 2209/131* (2013.01); *A61L 2209/132* (2013.01); *A61L 2209/135* (2013.01); *A61L 2209/14* (2013.01)

(58) Field of Classification Search
CPC . B05B 17/0607; B05B 17/0646; B05B 11/02; B05B 9/0861; B05B 11/3005; B05B 11/3007; B05B 11/3008; A61M 15/08; A61M 1/037; A61M 1/1058; A61M 11/00; A61M 11/02; A61M 15/0066; A61M 15/0065; F17C 1/00; F17C 1/005; F17C 7/00; F17C 7/02; B65D 83/262; B05C 17/0103; G01F 11/029; G01F 11/023; F41H 11/132
See application file for complete search history.

(56) References Cited

U.S. PATENT DOCUMENTS

| | | | |
|---|---|---|---|
| 4,627,385 A * | 12/1986 | Vinci | A01K 15/022 119/718 |
| 6,062,212 A * | 5/2000 | Davison | A61M 15/0085 128/200.16 |
| 6,149,873 A * | 11/2000 | Potter | A61L 9/12 239/271 |
| 6,390,453 B1 * | 5/2002 | Frederickson | A61M 15/02 261/100 |
| 6,425,350 B2 * | 7/2002 | Bulanda | A01K 15/02 119/712 |
| 6,531,145 B1 * | 3/2003 | Reichert | A01N 25/18 119/905 |
| 6,598,602 B1 * | 7/2003 | Sjoholm | A61M 11/005 128/200.14 |
| 6,840,197 B1 * | 1/2005 | Trompke | A01K 15/02 119/711 |
| 6,843,158 B2 * | 1/2005 | Garcia | A01K 15/02 102/403 |
| 7,334,541 B2 * | 2/2008 | Reiter | A01K 15/02 119/712 |
| 7,633,397 B2 * | 12/2009 | Dugan | G01N 33/0073 340/573.3 |
| 7,727,181 B2 * | 6/2010 | Rush | A61M 5/14216 604/67 |
| 7,976,794 B2 * | 7/2011 | Trump | G01N 35/109 222/52 |
| 8,187,533 B2 * | 5/2012 | Elrod | A61L 9/015 119/712 |
| 9,250,222 B2 * | 2/2016 | Furton | A01K 15/02 |
| 9,897,419 B1 * | 2/2018 | Reynolds | F41H 11/132 |
| 2002/0036358 A1 * | 3/2002 | Watkins | A61L 9/122 261/26 |
| 2005/0123420 A1 * | 6/2005 | Richter | F04B 43/043 417/413.2 |
| 2005/0268915 A1 * | 12/2005 | Wassenaar | A61M 15/009 128/206.11 |
| 2006/0075896 A1 * | 4/2006 | Andersson | A61L 2/183 96/227 |
| 2006/0144956 A1 * | 7/2006 | Ruetz | A61L 9/035 239/34 |
| 2009/0003855 A1 * | 1/2009 | Kubo | G03G 15/0907 399/44 |
| 2009/0038555 A1 * | 2/2009 | Reese | A01K 15/02 119/174 |
| 2009/0139459 A1 * | 6/2009 | Habacivch | A01K 15/02 119/420 |
| 2009/0196587 A1 * | 8/2009 | Cheung | A61L 9/037 392/394 |
| 2010/0089395 A1 * | 4/2010 | Power | A61M 15/0085 128/203.15 |
| 2010/0242859 A1 * | 9/2010 | Raymond | A01K 15/02 119/719 |
| 2010/0243754 A1 * | 9/2010 | Harris | A01M 1/2033 239/34 |
| 2010/0288627 A1 * | 11/2010 | Tanida | A61L 9/14 204/229.4 |
| 2010/0289655 A1 * | 11/2010 | Elrod | G01N 33/0039 340/632 |
| 2011/0030622 A1 * | 2/2011 | So | A01K 15/021 119/719 |
| 2011/0114744 A1 * | 5/2011 | Ricciardi | A61L 2/22 239/4 |
| 2011/0146588 A1 * | 6/2011 | Ward | A01K 15/02 119/712 |
| 2011/0203349 A1 * | 8/2011 | Reese | A01K 15/02 73/23.34 |
| 2012/0024042 A1 * | 2/2012 | Vass | G01N 33/0031 73/23.34 |
| 2012/0111285 A1 * | 5/2012 | Pearce | A01K 15/02 119/712 |

FOREIGN PATENT DOCUMENTS

| EP | 0398583 A2 * | 11/1990 | A61M 5/14224 |
|---|---|---|---|
| WO | WO-9901793 A1 * | 1/1999 | A61L 9/122 |

* cited by examiner

CONTROLLABLE SCENT SAMPLE DISPENSER, AND ANIMAL TRAINING AND TESTING SYSTEM FOR DETECTING SCENTS

CROSS-REFERENCE TO RELATED APPLICATION

This application is a continuation of copending International Application No. PCT/EP2011/057546, filed May 10, 2011, which is incorporated herein by reference in its entirety.

BACKGROUND OF THE INVENTION

The present invention relates to a (remote) controllable scent sample dispenser, the use of the remote controllable scent sample dispenser for supplying a scent sample with a predefined dosing rate to an animal's nose, a method for determining the minimum scent concentration of a scent sample an animal or an scent detection means can detect, and a method of positive-reinforced scent training an animal for reliable recognition of scent sample. In particular, the present invention relates to an animal training or testing system (ATS) for detecting a scent sample with a high reliability even if the scent samples have a very low scent concentration. Thus, the present invention generally relates to the field of training an animal, such as a dog, regarding scent detection and training.

In the field of scent detection by an animal, e.g. a dog, the scent detection training of the animal is usually based on hundred years old principles, mainly with the connection between a toy and a scent. Usually, a natural behavior of an animal is to search for his toy. If the scent sample is hidden in or with the toy, the searching behavior of the animal can be conditioned in that the animal could make his connection to a specific scent in order to search the scent.

In the field of scent detection by means of trained animals, the procedures of training the animals are directed to the goal to increase the scent detection reliability of a trained animal and to decrease the minimum scent concentration of a scent sample an animal can detect.

SUMMARY

According to an embodiment, a controllable scent sample dispenser may have: a microdosing device for outputting, during an activation state, a scent sample at a scent sample outlet to the environment, wherein the microdosing device is placeable adjacent to an animal's nose so that a distance between the outlet of the microdosing device and a nare or nostril of the animal's nose is within a predefined range, and a microdosing driver unit for adjusting a dosing rate of the scent sample output at the scent sample outlet by selectively activating the microdosing device.

Another embodiment may have use of the above remote controllable scent sample dispenser for selectively supplying a scent sample with a predefined dosing rate to an animal's nose.

According to another embodiment, a method of positive-reinforced scent training an animal for reliable recognition of a scent sample may have the steps of: supplying the scent sample to the nose of the animal to be trained, encouraging the animal to execute a specific behavior during exposing the animal's nose to the scent sample, rewarding the animal if it executes the specific behavior, and repeating the steps of supplying, encouraging and rewarding until the animal executes the specific behavior each time the scent sample is supplied.

According to another embodiment, a method for determining the minimum scent concentration of a scent sample, an animal can detect, may have the steps of: setting or calibrating the scent concentration of the scent sample provided by the scent reservoir, supplying the scent sample with a start dosing rate to the animal's nose, increasing the dosing rate supplied to the animal's nose, until the animal responds to the scent sample, wherein the minimum scent concentration detectable by the animal corresponds to the currently supplied dosing rate, when the animal responds to the supplied scent sample.

According to another embodiment, a method for determining the scent sample detection limit of an animal may have the steps of: setting or calibrating the concentration of the scent sample provided by the scent reservoir, supplying the scent sample with a start dosing rate to the animal's nose, decreasing the dosing rate supplied to the animal's nare, until the animal stops to respond to the scent sample, wherein the scent sample detection limit of the animal corresponds to the currently supplied dosing rate, when the animal stops to respond to the supplied scent sample.

According to another embodiment, a method for determining the minimum scent concentration of a scent sample, a scent detection means can detect, may have the steps of: setting or calibrating the scent concentration of the scent sample provided by the scent reservoir, supplying the scent sample with a start dosing rate to a sensing element of the scent detection means, increasing the dosing rate supplied to the sensing element, until the scent detection means responds to the scent sample, wherein the minimum scent concentration detectable by the scent detection means corresponds to the currently supplied dosing rate, when the scent detection means responds to the supplied scent sample.

According to still another embodiment, a method for determining the scent sample detection limit of a scent detection means may have the steps of: setting or calibrating the concentration of the scent sample provided by the scent reservoir, supplying the scent sample with a start dosing rate to a sensing element of the scent detection means, decreasing the dosing rate supplied to the sensing element, until the scent detection means stops to respond to the scent sample, wherein the scent sample detection limit of the scent detection means corresponds to the currently supplied dosing rate, when the scent detection means stops to respond to the supplied scent sample.

The present invention is based on the finding that the training of animals for detecting and recognizing minute concentrations of scent samples with a very high reliability can be improved by bringing a predefined quantity per time unit (dosing rate) of a specific scent sample in immediate proximity to the nose or nare (nostril) of the animal to be trained, e.g. a dog. In this connection, it is pointed out that any animal which has a sufficient sensitivity to detect specific scent samples and, for example, a minute dose of such a scent sample, and which can be trained to show or execute a specific, predetermined behavior, when recognizing the specific scent sample, can be employed in accordance to the teachings of the present invention.

In order to supply the scent sample with a very precise and accurate dosing rate to the animal's nose, the outlet of the microdosing device, which may be implemented for example by means of a micropump or micro membrane pump, is fixed to the animal's head so that a distance between the outlet of the microdosing device and a nare of the animal's nose is within a predefined range having a possible extension of 0 to 5 cm. Alternatively, the scent sample may be directly supplied into the nare of the animal's nose by placing the outlet of the microdosing device (e.g. over a tubing element) in the nare of the animal's nose.

According to the inventive concept, the scent sample dispenser may comprise a microdosing device fluidically coupled to a scent sample reservoir and a scent sample outlet, the microdosing device being configured to create during an activation state, a flow of a carrier gas (i.e. a carrier gas stream) through the scent sample reservoir for taking up particles (e.g. in form of molecules, liquid droplets and/or fine solid particles) of the scent (fluid) sample into the carrier gas, and to output a scent (fluid) sample in form of the carrier gas with the scent sample particle at the scent sample outlet to the environment. A microdosing driver unit is configured to adjust the dosing rate of the scent sample output at the scent sample outlet by selectively activating the microdosing device. Thus, according to inventive scent sample dispenser, scent sample particles or molecules or droplets stored in a scent sample reservoir are provided to a carrier gas, wherein, for example, the carrier gas is sucked in from the environment and filtered by an adequate filter element. The flow of the carrier gas is guided through the reservoir so that the carrier gas can take up the particles of the scent sample stored in the reservoir.

Thus, the inventive scent (fluid) sample dispenser or scent dosing system can use high performance micropumps achieving a pumping rate up to 350 ml/min with air, and a back pressure ability of 25 kPa. Even small silicon micropumps with a chip size of e.g. 7×7×1 mm$^3$ achieve gas pump rates of up to 40 ml/min. Next, with peristaltically driven plastic micropumps, pump rates of up to 30 ml/min are achievable. With that, using new and powerful micropumps, it will be possible to transport the scent sample molecules dissolved in air directly via an outlet of the microdosing device through the air, e.g. over a distance of up to about 10 cm or more, to the animal's nose.

Next, at the outlet of the dispenser a nozzle with a diameter between e.g. 5 μm and 100 μm can be arranged, to increase the flow velocity of the scent/air sample flow to bridge the gap between scent sample outlet and the animal's nose.

Due to the very high dosing precision of micro-membrane pumps available at present, a dosing precision of the scent sample with minute volume quantities, such as, for example 1 nl to 10 μl are achievable per pump stroke.

By supplying the scent sample to be detected by the animal with a very high dosing accuracy and within very precisely definable time intervals or periods, any animal training and testing method for detecting and recognizing scent samples can be performed with a very high training and testing efficiency. In particular, the inventive animal training and testing system allows to control the operation of the inventive scent sample dispenser by the operator, such as an animal trainer, on a remote basis. To be more specific, the microdosing driver unit for selectively activating the microdosing device may be implemented for receiving the control signals from a remote system controller operated by the operator. Thus, the signal receiving element of the microdosing driver unit may be configured to install a wireless connection to the remote system controller or, alternatively, a wired connection may be implemented, for example, in the leash, which is held by the operator, to the animal's collar.

Using the inventive scent sample dispenser which delivers a very small amount of the scent sample with a very high dosing accuracy and within very precisely definable timing intervals or periods, the scent impression can be controlled to appear only for short intervals as the scent impression will disappear immediately within a few seconds by diffusion. Thus, after a few seconds the animal cannot smell the old (previously supplied) scent anymore. Now, a new (e.g. different) scent can be delivered to the animal. Moreover, the intensity of the supplied scent sample may be easily adjusted or adapted.

According to the inventive scent sample dispenser, a sufficiently powerful microfluidic actuator may pump a gaseous medium (air and scent), from a reservoir with a scent source comprising or providing the scent molecules, in immediate proximity to the animal's nose as the flow rate of the microfluidic actuator is strong enough to carry the scent molecules outside the reservoir directly to the outlet of the microdosing device and to the nostril of the animal's nose.

In order to avoid that the animal reacts to the noise or sound, the mechanical vibrations or the air/gas draught generated by the scent sample dispenser when the scent sample is supplied to the environment, a dummy dispenser may be arranged in immediate vicinity to the remote controllable scent sample dispenser. The dummy dispenser is formed to generate, during activation, essentially the same noise or sound, the same mechanical vibration and the same air or gas draught as the controllable scent sample dispenser. The dummy dispenser may be randomly (e.g. sporadically or intermittently) activated during the time periods, the controllable scent sample dispenser is not activated, so that the animal to be trained does not associate the noise or sound, the mechanical vibrations, and/or the air or gas draught of the controllable scent sample dispenser to the release or supply of the scent sample to the environment. The controllable scent sample dispenser and the dummy dispenser may be activated by the remote system controller of the animal trainer, wherein as an alternative option, the dummy dispenser may be activated by the microdosing driver unit for example by means of a software routine controlling the time intervals for activating the dummy dispenser.

BRIEF DESCRIPTION OF THE DRAWINGS

Embodiments of the present invention will be subsequently described in detail referring to the appended drawings, in which.

DETAILED DESCRIPTION OF THE INVENTION

Before discussing the present invention in further detail using the drawings, it is pointed out that in the figures identical elements and elements having the same functionality or the same effect are provided with same reference numbers so that the description of these elements and the functionality thereof illustrated in the different embodiments is mutually exchangeable or may be applied to one another in the different embodiments.

Subsequently, a first general embodiment of a scent sample dispenser 10 for supplying a scent sample with a precisely adjusted dosing rate to the immediate proximity of an animal's nose or nare will be described using FIGS. 1a-b for a general discussion of the functional context.

Figure 1A:
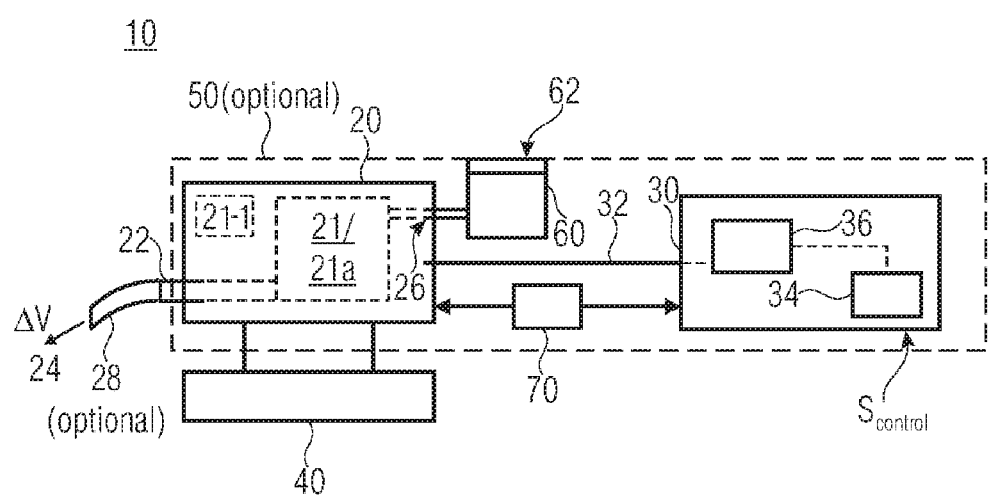
FIG. 1a-b show principle illustrations of the functional groups of the remote controllable scent sample dispenser in accordance with an embodiment of the present invention.

As depicted in FIG. 1a, the remote controllable scent sample dispenser 10 comprises a microdosing device 20 having a scent sample outlet 22, a microdosing driver unit 30 at least electrically and, as an option, mechanically coupled to the microdosing device 20, and a fixing element 40. As an optional measure, FIG. 1a shows an optional, common housing for the microdosing device 20 and the microdosing driver unit 30, wherein the fixing element 40 is, in case of the presence of the common housing 50, attached to the common housing 50. It should become clear that the microdosing device 20 and the microdosing driver unit 30 may also be implemented as separate functional groups and may be housed in different housings (not shown in FIG. 1a). In this case, at least the fixing element 40 is attached to the microdosing device 20.

The microdosing device 20 comprises a scent sample outlet 22 for outputting, during an activated state of the microdosing device 20, a scent sample 24 to the environment. The microdosing driver unit 30 is configured for adjusting a dosing rate of the scent sample 24 output at the scent sample outlet 22 by selectively activating the microdosing device 20. Thus, the microdosing driver unit 30 may be connected by means of a control line 32 with the microdosing device 20 for providing electrical control signals to the microdosing device 20.

Optionally, a scent sample reservoir 60 may be fluidically coupled to an inlet 26 of the microdosing device 20. The optional reservoir 60 may be located externally or internally to the microdosing device 20. Moreover, the scent sample reservoir 60 may for example comprise an elastic sidewall so that no negative pressure arises during emptying, and optionally has a septum and/or an inlet port (not illustrated in FIG. 1a) for filling or refilling the reservoir 60 with the scent sample material. Moreover, the reservoir 60 may be implemented as a fluid channel separated by means of a filter element 62 from the environment wherein the fluidic channel comprises, for example, a piece of a scent creating material so that scent molecules are dissolved in a gas, for example air, provided through the filter element from the environment.

The filter element may be an active carbon filter. The filter element may filter out potential contaminations or other undesired substances from the environment and may also prevent molecules of the scent sample from leaking to the environment. In order to avoid an uncontrolled flow of the scent sample from the reservoir 60 through the microdosing device 20 to the outlet 22, a so-called free flow protection may be arranged in the fluid channel downstream to the scent sample reservoir 60. The free flow protection may be, for example, implemented as a pre-tensioned diaphragm. Thus, the scent sample reservoir 60 may be configured to provide the scent sample 24 to the microdosing device 20 with a specific scent concentration in the form of scent molecules dissolved in filtered air.

According to embodiments of the present invention, the microdosing device 20 comprises a micropump 21 with a pump chamber 21a providing a stroke volume $\Delta V$. In micro membrane or micro-diaphragm pumps, the membranes or diaphragms (micro-membranes or micro-diaphragms) are driven by a predetermined or adjustable pump stroke or diaphragm excursion for transporting the fluid (scent sample) in a predetermined direction. For example, a piezoelectric element which may be enabled electrically, may exemplarily be used as micropump or micro membrane pump of the microdosing device 20 according to an embodiment of the present invention. Depending on the electrical excitation, the stroke volumes of micro membrane or micro diaphragm pumps may exemplarily be generated in a range from 1 nl to 10 µl (or more) per pumping stroke.

In order to achieve a high dosing accuracy of the scent sample 24 when supplying the scent sample 24 to the immediate proximity of the animal's nose, the so-called dead volume of the micropump should be as low as possible. The dead volume of the micropump extends between an exit of the pump chamber and the outlet 22 of the micropump. Thus, for achieving a high accuracy the dead volume of the micropump of the microdosing device 20 should be, for example, less than 20- or 10-times of the stroke volume.

In case, the microdosing device 20 comprises a tubing element 28 as the scent sample outlet 22 for supplying the scent sample 24 in an immediate proximity to the nose or nare of the animal, the tubing element 28 should be as short as possible, so that the volume of the tubing element 28 is for example less then 5- or 3-times the stroke volume.

According to a further embodiment of the present invention, the microdosing device 20 may comprise a further micropump element 21-1, which may be continuously activated in order to suppress vibrations or noise from the "first" micropump or, alternatively, may be randomly activated by the microdosing driver unit during time periods, the first micropump is not activated. Usually, the further micropump 21-1 has the same design as the first micropump and do not provide a pumping function. The function of the further micropump 21-1 is either to suppress the noise, the sound or the vibrations of the first micropump during activation or to randomly activate the micropump, in order to avoid that the animal associates the noise/sound or the vibrations of the first micropump to the scent sample supply. Thus, the animal will not react to the activation of the first micropump as the training result but (essentially only) to the supply of the scent sample 24 to the animal's nose.

The microdosing driver unit 30 is, for example, configured to activate the microdosing device 20 responsive to a control signal $S_{control}$ received from an operator or animal trainer. The microdosing driver unit 30 may comprise a wireless receiver 34 for installing a wireless connection to the remote control (not shown in FIGS. 1a-b) of the operator. Thus, the operator can control the supply of the scent sample 24 to the animal's nose over a wireless connection to the microdosing driver unit 30 of the remote controllable scent sample dispenser 10. Alternatively, the microdosing driver unit 30 of the sample dispenser 10 may be connected to the remote system control of the animal trainer by means of a signal line and optionally a power supply line integrated to a leash which may be mechanically coupled to a neck collar of the animal. Thus, the microdosing driver unit 30 may be arranged on the neck collar (not shown in FIGS. 1a-b) of the animal and may be connected over the signal line 32 to the microdosing device 20. Moreover, the remote controllable scent sample dispenser 10 may comprise a power supply element 70 for example in the form of a replaceable battery or a rechargeable battery. The power supply element in form of the battery 70 may be integrated to the microdosing driver unit 30, the microdosing device 20 or the fixing element 40 and electrically coupled to the microdosing device 20 and/or the microdosing driver unit 30.

Alternatively, the necessitated power for energizing the microdosing device 20 and the microdosing driver unit 30 may be supplied over a power supply line which may be integrated into a leash attached to the animal's neck collar and held by the animal trainer. Thus, as an alternative option, the power supply element may be integrated into the remote system controller held by the animal trainer.

Further designs and additional functional elements which may optionally be added to the remote controllable scent sample dispenser 10 illustrated in FIG. 1a and the functionality thereof in cooperation with the functional elements described before will be subsequently described referring to FIG. 1b.

Figure 1B:
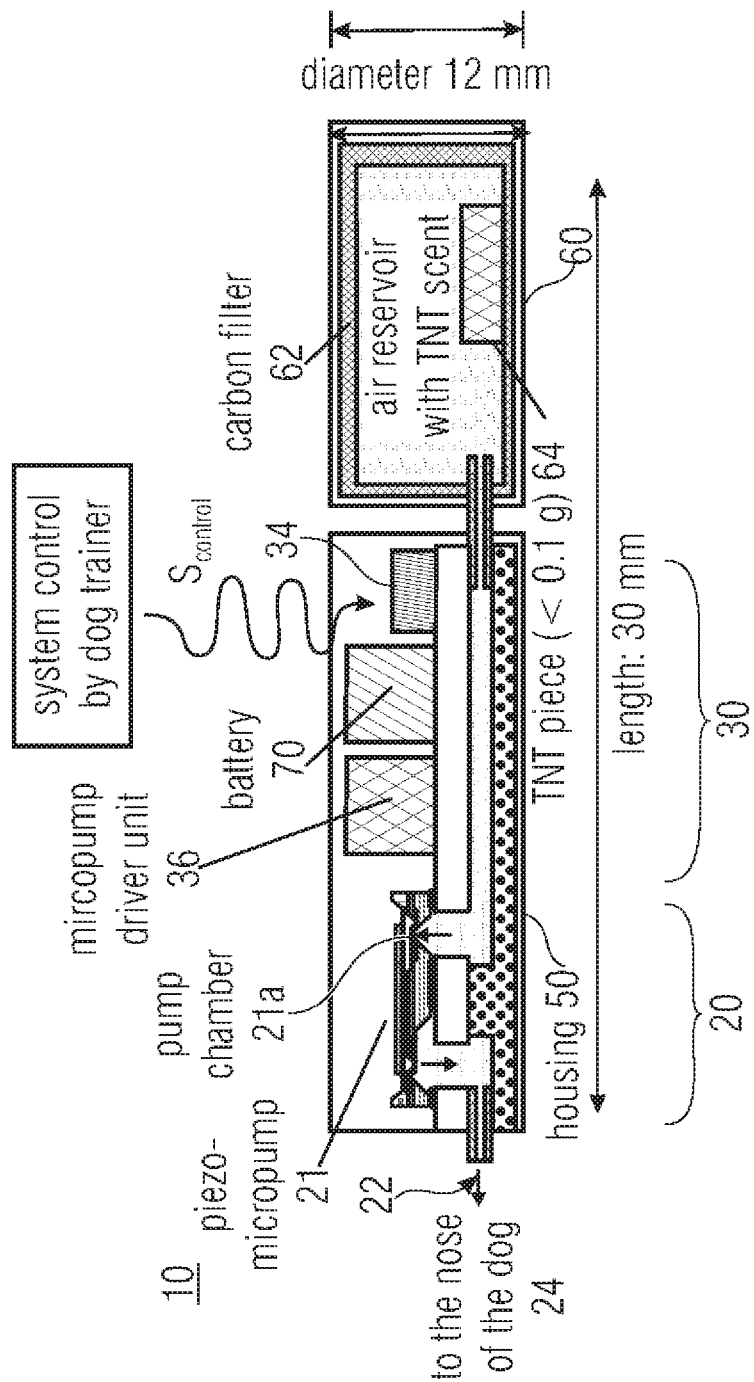

As it is depicted in FIG. 1b, the remote controllable scent sample dispenser 10 exemplarily comprises the microdosing device 20 in form of a piezo-micropump 21 for outputting, during an activated condition, the scent sample 24 at the scent sample outlet 22 to the environment. The microdosing driver unit 30 which is integrated to a common housing 50 with the microdosing device 20 comprises the micropump driver unit 36, the battery 70 and the wireless receiving element 34. Furthermore, a scent sample reservoir 60 is fluidically coupled to the piezo-micropump 20. The reservoir 60 contains a piece 64 of a scent creating material such as in form of a TNT piece. Moreover, the reservoir 60 comprises a filter element 62 which is pervious to gas of the environmental atmosphere, but avoids leaking of the scent sample 24 from the reservoir 60 to the environment.

As outlined in FIG. 1b, exemplary outer dimensions of the housing 50 of the remote controllable scent sample dispenser 10 are, for example, 30 mm in length and 12 mm in diameter.

As outlined in FIG. 1b, the reservoir comprises a TNT piece (e.g. <0.1 g) as the scent creating material 64, wherein scent molecules of the TNT material are dissolved in air and, during activation of the microdosing device 20 in form of a piezo-micropump 21, are supplied to the scent sample outlet 22. It is to be kept in mind in this context that the scent creating material 64 arranged in the reservoir 60 may be any material on the field of security or medical applications which an animal may detect, for example, detection work in mine and UXO (UXO=Unexploded ordnance) detection, roadside bomb detection, explosive detection, narcotic detection, contraband detection, cancer detection, virus/bacteria detection, and detection of goods which are generally dangerous for humans.

To summarize, the storage volume of the reservoir 60 may comprise a solid material as a scent sample carrier. Based on the active surface of the scent sample carrier, the temperature T in the scent sample reservoir 60, the scent sample carrier will dispense scent sample molecules to the inner volume of the scent sample reservoir 60 until an equilibrium concentration c of the scent sample 24 in form of scent sample molecules dissolved in a gas will be present in the inner volume of the scent sample reservoir 60. Thus, a defined concentration c (c=N/V with N is the amount of molecules, and V is the value of the inner space) of the scent sample 24 is adjustable within the inner volume of the scent sample reservoir 60. The concentration c can be adjusted (increased or decreased) by changing (increasing or decreasing) the temperature of the scent sample (respectively solid sample material) with a heater element (increasing) or cooling element (decreasing). As a further alternative, a predefined concentration of the scent sample 24 may be achieved within the inner volume of the scent sample reservoir 60 by arranging a scent sample carrier having a liquid phase and a predefined mass. After heating the scent sample carrier, all molecules of the scent sample will be in a gaseous phase for achieving a specific, predefined concentration c of the scent sample within the inner volume of the scent sample reservoir 60. In order to avoid a recondensation of the scent sample at the walls of the reservoir, the walls of the reservoir 60 should be heated to a wall temperature exceeding a recondensation temperature of the scent sample. Thus, a predefined amount of molecules of the scent sample is within the inner volume of the scent sample reservoir 60. To summarize, based on the quantity (or volume) of the scent sample carrier and the resulting surface thereof effective for emitting or dispensing scent sample particles to the inner volume of the reservoir 60, the concentration c of scent sample particles in the inner volume is precisely adjustable to a desired, predefined concentration value c.

With that, the concentration c of the scent particles or molecules is known or can be detected and/or adjusted principally. Based on a precise microdosing element (e.g. a micropump with a stoke volume $\Delta V$) which can transport a defined volume from the scent sample reservoir, a precise and accurate dosing of a scent sample to the nose of an animal can be realized.

Due to the minute dead volume of the microdosing device 20 used for the inventive scent sample dispenser 10, the scent sample can be supplied to the environment (e.g. the animal's nose) immediately (i.e. essentially without any delay) after a received activation signal and, also, with a very precise dosing rate. For example, the (approximate) number $N_1$ of scent sample particles supplied to the environment can be calculated and, thus, adjusted as follows: $N_1 = c * n * \Delta V$, wherein "c" is the concentration of the scent sample particles in the reservoir (and, respectively, in the carrier gas at the scent sample outlet), wherein "$\Delta V$" is the stroke volume of the micropump of the microdosing device 20, and wherein "n" is the number of pump strokes or diaphragm excursions for transporting the carrier gas in a predetermined direction.

The scent sample creator may be a solid body (solid state material) or a liquid material for providing the scent sample molecules to the inner volume of the scent sample reservoir 60. In case the scent sample creating material is a solid body or a solid state material, the provision of the scent sample molecules in the inner volume of the scent reservoir 60 may be achieved by releasing particles or molecules or droplets of a substance from or through a surface of a solid body or solid state material containing the substance (e.g. due to the desorption phenomenon). In case the scent sample creating material 64 is present in form of a liquid material, the liquid material may be vaporized by heating to provide the defined concentration of scent sample molecules in the inner volume of the scent sample reservoir 60. Moreover, as a further alternative, the scent sample molecules may be present already in a gaseous form with a defined concentration c within the inner volume of the scent sample reservoir 60. Thus, the scent sample reservoir 60 can be a (fixed or replaceable) scent sample container or cartridge.

In the context of the present invention, it is described that particles or molecules of the scent sample are supplied to the carrier gas to form the scent sample which is output at the scent sample outlet to the environment. It should become clear that the term "particles" usually refers to (e.g. microscopic) particles of sizes ranging from atoms to molecules or groups/clusters of molecules. For example, the carrier gas having taken up or dissolved therein the scent sample particles can also be referred as an "aerosol" which is a suspension of fine solid particles or liquid droplets in a gas or carrier gas, wherein the carrier gas is, for example, filtered air supplied from the environment. Thus, the term particles is used synonymously for liquid droplets, molecules and/or fine solid particles of the scent sample in the present specification.

With respect to the above embodiments, the scent sample outlet 22 may comprise a nozzle or a nozzle structure (not shown) for increasing the flow speed of the scent sample 24 output at the scent sample outlet 22 to the environment. The nozzle or nozzle structure may be integral to the scent sample outlet 22 or may be a separate element securely fixed to the scent sample outlet 22.

The nozzle or nozzle structure associated to the scent sample outlet 22 may be any element decreasing the cross-sectional area of the fluid path at the scent sample outlet 22. Thus, the nozzle or nozzle structure may be implemented by a bottleneck-shaped section of the scent channel at the scent sample outlet 22. The nozzle or nozzle structure may be a thin metal plate having an orifice (e.g. etched, or laser drilled), a small silicon chip with an KOH etched or dry etched orifice, a pipe or tube of varying cross-sectional area and it can be used to direct or modify the flow of the scent sample 24 output at the scent sample outlet 22 to the environment. Thus, such a nozzle or nozzle structure can be used to control the rate of flow, speed, direction, mass, shape and/or the pressure of the scent sample stream that emerges therefrom. In order to avoid an unnecessary increase of the dead volume of the inventive scent sample dispenser, the nozzle or nozzle structure can be integrally incorporated into the scent sample outlet 22 or the tubing element 28 (if present). Practically, the nozzle or nozzle structure at the scent sample outlet may be a decrease of the cross-sectional area of the fluid channel by approximately 20 to 95% (or 40 to 60%). However, it should be ensured that the utilization of a nozzle or nozzle structure does not affect the functionality or efficiency of the microdosing device 20 when creating the flow of the carrier gas. Thus, the chosen nozzle type may depend on the design of the respectively used micropump.

Another embodiment to adapt the nozzle to the microdosing element like a silicon or metal micropump is to adapt the nozzle chip directly to the outlet of the silicon chip, that means that the nozzle is adapted at the bottom side of the micropump chip (e.g. by Silicon Fusion Bond, by gluing or by laser welding), and the pump chip is arranged in a way that the nozzle is directed to the animal's nose. With that the dead volume between outlet valve of the pump and nozzle can be reduced to less than 0,2 µl (e.g. dry etched valve, size of the outlet valve hole e.g. $0,5 \times 1,0 \times 0,4$ m$^3$=0,2 mm$^3$=0,2 µl). Another advantage of this embodiment is that not only the dead volume, but also the fluidic capacitances of the outlet 22 is very small due to the stiff materials (silicon, metal), with that very small amounts of scent samples can be dispensed and changed very quickly.

Based on the increase of the flow velocity of the scent sample outlet 22, greater distances from about 10 cm (e.g. 5 to 15 cm or 8 to 12 cm) between the scent sample outlet 22 and the animal's nose may be bridged. Thus, the inventive scent sample dispenser 10 may be arranged in a greater distance from the animal's nose so that a greater acceptance of the dispenser by the animal may be achieved without any deterioration of the desired/adjusted dosing rate.

Moreover, all parts and functional elements of the remote controllable scent sample dispenser shown in FIG. 1a-b and, also, the materials used therefore should be designed to avoid and suppress (as far as possible) any undesired leaking or diffusion of components of the scent sample to the environment.

As shown in FIG. 1a-b, the scent sample reservoir is arranged upstream to the microdosing device 20 having the micropump 21, so that the microdosing device 20 sucks the scent sample from the scent sample reservoir 60 and through connecting tubing elements and supplies the precisely dosed scent sample at the scent sample outlet 22 to the environment. Alternatively, the scent sample reservoir 60 may be arranged downstream to the microdosing device 20, so that the microdosing device 20 may supply the scent sample to the environment by pushing air or gas through the scent sample reservoir 60 and then through the scent sample outlet 22 to the environment.

Subsequently, another alternative implementation of the inventive remote controllable scent sample dispenser 10 in accordance with another embodiment will be discussed making reference to FIG. 2. With regard to the further description based on FIG. 2, it is pointed out that the elements of the remote controllable scent sample dispenser 10 which are identical in their function and have the same function or the same effect as those elements of the scent sample dispenser illustrated in FIGS. 1a-b, are still provided with the same reference numbers.

Figure 2:
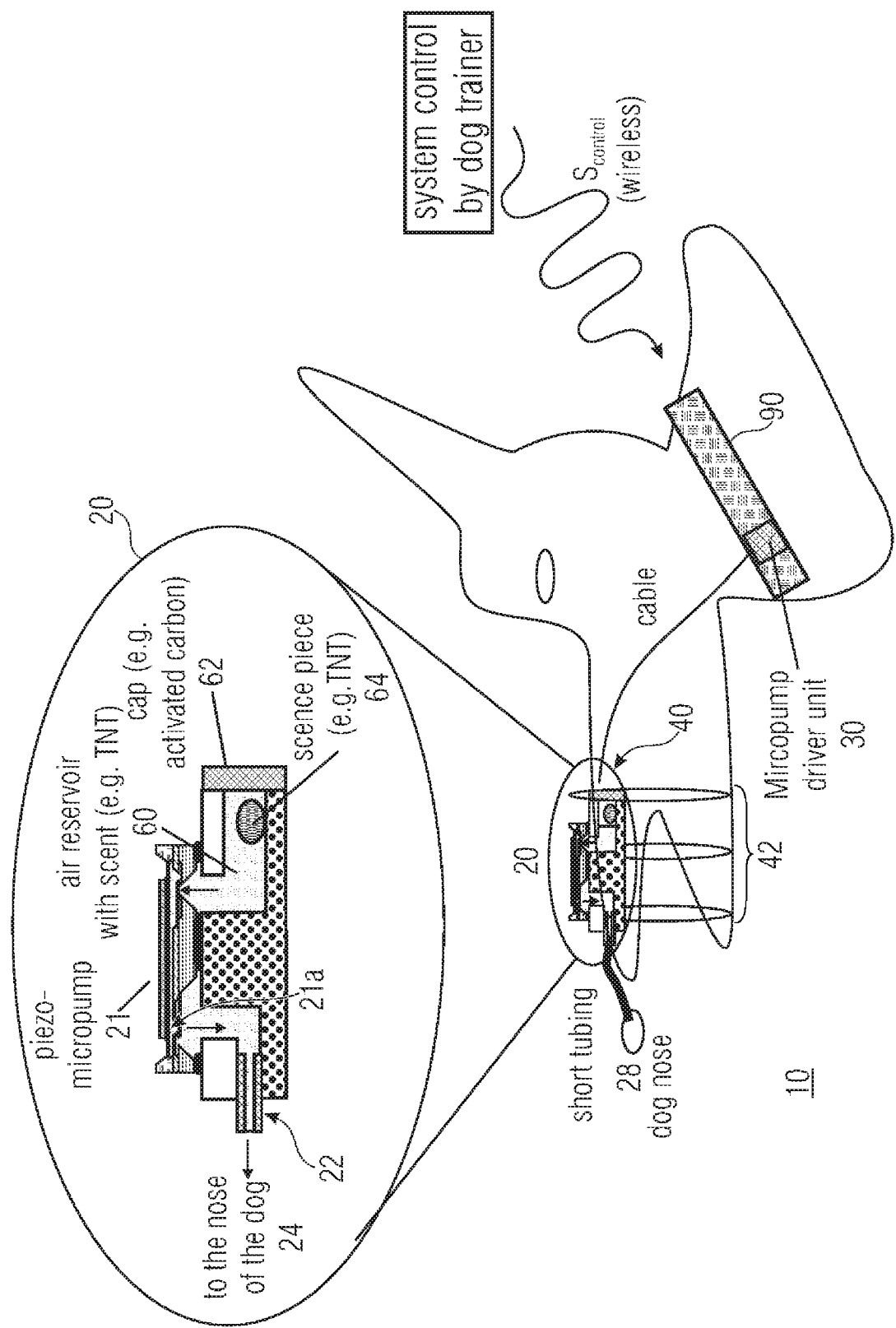
FIG. 2 shows a principle illustration of a scent sample dispenser applied to a dog in accordance with another embodiment of the present invention.

As it is depicted in FIG. 2, the microdosing device 20 of the scent sample dispenser 10 is fixed by means of a fixing element 40 which is for example part of a muzzle 42 attached to the animal's head, adjacent to an animal's nose, so that a distance between the outlet 22 of the microdosing device 20 and a nare of the animal's nose is within a predefined range, which is for example less than 5 or 2 cm. Alternatively, the scent sample may be directly supplied into the nare of the animal's nose by placing the outlet of the microdosing device (e.g. a tubing element) in the nare of the animal's nose. As outlined in FIG. 2, the microdosing driver unit 30 is arranged on a neck collar 90 of the animal and electrically connected to the microdosing device 20 by means of the signal line 32.

As outlined in the enlarged section of FIG. 2 with respect to the microdosing device 20, it is shown that the microdosing device 20 for example comprises a piezo-micropump 21 in form of a micro membrane or micro diaphragm pump, which is fluidically coupled to the scent sample reservoir 60. As shown in FIG. 2, the scent sample reservoir comprises the scent creating material piece 64, wherein at least one sidewall of the reservoir 60 having a cap comprises an activated carbon material as the filter element 62 to the environment.

In the following, the principle functionality of the remote controllable scent sample dispenser 10 and the inventive utilization of the described scent sample dispenser 10 as well as the inventive animal testing and training procedures based on the inventive scent sample dispenser 10 are described in detail.

To be more specific, the inventive remote controllable scent sample dispenser 10 can be utilized for selectively supplying a scent sample 24 with a predefined dosing rate to an animal's nose. This precise scent sample supply to an animal's nose allows an animal trainer to train and test the animal's scent detection reliability and accuracy in a very efficient way. Thus, based on the defined distance between the outlet of the microdosing device and the animal's nose, and also on the very precise dosing rate, very expressive and comparable training and testing conditions can be achieved for training or testing and for comparing the minimum detection concentration of the animals to be trained and employed on security or clinical (medical) applications.

Thus, the inventive remote controllable scent sample dispenser 10 can be used to measure the lowest possible detection rate that an animal can smell or detect. Moreover, the inventive remote controllable scent sample dispenser 10 can support new training principles mainly by bringing very precise dosing rates of the scent sample 24 from the scent reservoir 60 to the animal's nose by a microdosing device 20, e.g. in form of a micropump 21. The microdosing device 20 may be remote controlled over the microdosing driver unit 30, wherein the microdosing device 20 and, for example, the microdosing driver unit 30 may be fixed together adjacent to the animal's nose so that a distance between an outlet 22 of a microdosing device and a nare of the animal's nose is within a predefined range, e.g. less then 2 cm. Alternatively, only the microdosing device 20 is placed adjacent to the animal's nose, wherein the microdosing driver unit 30 is, for example, attached to a neck collar 90 of the animal.

The fixing element 40 for fixing at least the microdosing device 20 and, optionally, the microdosing driver unit 30 adjacent to the animal's nose may be implemented as a part of a muzzle 42 attached to the animal's head. Thus, during an activation of the microdosing device 20, the scent sample 24, e.g. in form of scent molecules dissolved in air, can selectively be supplied with a very precise, predefined dosing rate to the animal's nose. In order to activate the remote controllable scent sample dispenser 10, the animal trainer may activate the remote system controller (not shown in FIG. 2), for example by pushing a button, wherein the control signal $S_{control}$ is transmitted to the microdosing driver unit 30, which is for example attached to the animal's neck collar 90, by means of a wireless signal or by means of a line-coupled signal over a signal line in the leash held by the animal trainer and attached to the neck collar of the animal. Due to the activation signal, the microdosing device 20 outputs with a precise dosing rate the scent sample 24 to the environment next to the animal's nose.

In order to avoid that the animal reacts to the noise or the vibrations of the micropump 21 during activation, but not to the supplied scent sample 24, a second (e.g. identically designed) micropump (not shown in FIG. 2), producing essentially the same sound and vibrations as the first micropump 21, will be arranged in the microdosing device 20. The second micropump may be activated by the microdosing driver unit 30 continuously in order to suppress the noise and the vibrations of the actually running micropump however, without releasing any scent sample. Alternatively, the second micropump may be randomly activated during time periods, the first micropump is not activated, so that the animal to the trained does not associate the noise or the vibrations of the first micropump 21 to the release or supply of the scent sample 24.

As an alternative embodiment, a further dispenser arrangement ("a dummy dispenser") comprising at least the same mechanical parts and having essentially the same mechanical structure as the remote controllable scent sample dispenser 20, may be arranged immediately adjacent to the controllable scent sample dispenser. For example, the dummy dispenser may be an exact (1:1) copy of the remote controllable scent sample dispenser 20.

In order to avoid that the animal reacts to the noise or sound, the mechanical vibrations or the air or gas draught generated by the scent sample dispenser at the outlet when the scent sample is supplied to the environment, the dummy dispenser is arranged in an immediate vicinity to the controllable scent sample dispenser. The dummy dispenser is formed to generate, during it's activation, essentially the same noise or sound, the same mechanical vibration and the same air or gas draught as the controllable scent sample dispenser. Thus, the dummy dispenser may be placed immediately adjacent to the controllable scent sample dispenser so that the animal to be trained cannot distinguish between a training state when only the controllable scent sample dispenser is activated, and a dummy state when only the dummy dispenser is activated. Moreover, the (adjustable) timing ratio between the training states and the dummy states may be selected so that the resulting activation duration of the dummy dispenser is at least 5, 10, 20, 50 or 100 times longer then the resulting activation duration of the remote controllable scent sample dispenser 20. The resulting activation duration of the dummy dispenser is the sum of the time periods the dummy dispenser is activated, wherein the resulting activation duration of the remote controllable scent sample dispenser is the sum of the time periods the remote controllable scent sample dispenser is activated.

The dummy dispenser may be activated by the microdosing driver unit continuously in order to suppress the noise or sound, the mechanical vibrations and the air or gas draught of the actually running scent sample dispenser, however, without releasing any scent sample. Alternatively, the dummy dispenser may be randomly (e.g. sporadically or intermittently) activated during the time periods, the controllable scent sample dispenser is not activated, so that the animal to be trained can not associate the noise or sound, the mechanical vibrations, and/or the air or gas draught of the controllable scent sample dispenser to the release or supply of the scent sample to the environment. The controllable scent sample dispenser and the dummy dispenser may be activated by the remote system controller of the animal trainer, wherein as an alternative option, the dummy dispenser may be activated by the microdosing driver unit for example by means of a software routine controlling the time intervals for activating the dummy dispenser.

In case, the scent sample is directly supplied into the nare of the animal's nose by placing the outlet 22 (or the tubing element 28) of the remote controllable scent sample dispenser 10 in the nare of the animal's nose, the outlet (or a corresponding tubing element) of the dummy dispenser is also placed (adjacent to the outlet 22 or the tubing element 28) in the nare of the animal's nose.

The first and second micropump of the microdosing device 20 may be activated by the remote system controller of the animal trainer, wherein as an alternative option, the second micropump may be activated by the microdosing driver unit 30 for example by means of a software routine controlling the time intervals for activating the second micropump.

As the stroke volumes $\Delta V$ of micropumps may be adjusted based on the electrical excitation, the remote system controller of the animal trainer may be equipped with different leveling means for adjusting the dosing rate (quantity per time unit) of the scent sample 24 supplied to the animal's nose. Moreover, the time intervals for activating the microdosing device 20 may be adjusted over the remote system controller or a software routine implemented therein. To be more specific, the remote system controller may be equipped with a computer software for executing different training and testing routines which can be adapted to different training levels of different animals and/or to different training concepts for different kinds of animals.

During activation, the micropump of the microdosing device 21 supplies the scent sample 24 from the reservoir to the animal's nose, wherein the scent sample comprises the scent molecules dissolved in air. As shown in FIG. 2, the microdosing driver unit 30 is arranged at the neck collar 90 of the animal, wherein the microdosing device 20 is arranged adjacent to the animal's nose. According to the present invention, the fixing element 40 for fixing the microdosing device 20 adjacent to the animal's nose may be a part of a muzzle 42 attached to the animal's head or may be a specially designed muzzle 42. As shown in FIG. 2, the overall size of the remote controllable scent sample dispenser 10, comprising for example two micropumps, a carrier substrate, the reservoir chamber, a carbon filter, may be implemented with very small dimensions, and advantageously with a volume of less than two cubic centimeters. In order to keep the dimensions of the scent sample dispenser 10 low, the air reservoir 60 is located next to the microdosing device 20 or is integrated to the microdosing device 20. Moreover, in order to prevent leaks and unnecessary dead volumes, a tubing element 28 at the scent sample outlet 22 of the microdosing device 20 should be kept short for providing a low tubing volume.

The following evaluations relate to the so-called dead volume of the microdosing device 20. According to the present invention, the dead volume between the exit of the micropump 21 and the nose of the animal should be as small as possible. Taking into account that the micropump 21 can deliver small quantities very accurately, e.g. with an exemplary stroke volume of 0.25 µl, the air volume containing the scent molecules (e.g. the scent sample) should be transported immediately to the nose. The following estimation show a possible dead volume of a microdosing device:

TABLE 1

|  | Length (mm) | Cross section (mm$^2$) | Dead volume [µl] |
| --- | --- | --- | --- |
| Dead volume inside the silicon pump chip | 0.5 | 5 | 2.5 |
| Dead volume inside the silicone gasket | 0.2 | 5 | 1.0 |
| Dead volume inside the outlet hole of the carrier | 5.0 | 0.5 | 2.5 |
| Dead volume of the tubing (ID* 0.2 mm) | 40 | 0.04 | 1.6 |
| Total Dead volume between pump and nare |  |  | 7.6 |

*inner diameter

As a result of the above dimensions of the dead volume and a total dead volume of about 7.6 µl, the microdosing device must pump nearly 30 pump strokes, until the first scent appears to the nare of the animal's nose. Therefore, when performing training and testing procedures for the scent detection with animals, the dosing accuracy is not limited by the stroke volumes or the accuracy of the micropump 21, but by the total dead volume between the micropump 21 of the microdosing device 20 and the animal's nare.

Thus, the following measures can be taken to reduce the total dead volume:
Grinding the bottom wafer for reducing the thickness (e.g. from 450 µl to 100 µl,
Reducing the thickness of the gasket (e.g. to 50 µl,
Reducing the length of the hole (e.g. to 1 mm),
Reducing the length of the tubing element (e.g. to 20 mm).

Based on the above measures, the total dead volume can be drastically reduced. The following Table 2 shows exemplarily changed dimensions.

TABLE 2

|  | Length (mm) | Cross section (mm$^2$) | Dead volume [µl] |
| --- | --- | --- | --- |
| Dead volume inside the silicon pump chip | 0.1 | 5 | 0.5 |
| Dead volume inside the silicone gasket | 0.05 | 5 | 0.25 |
| Dead volume inside the outlet hole of the carrier | 1.0 | 0.5 | 0.5 |
| Dead volume of the tubing (ID* 0.1 mm) | 40 | 0.01 | 0.4 |
| Total Dead volume between pump and nare |  |  | 1.65 |

*inner diameter

Thus, only seven pump strokes are needed to pump the scent sample to the animal's nare. A further alternative arrangement is to arrange the outlet of the silicon chip directly in front of the animal's nare. However, the fixing element or the muzzle as part of the fixing element have to be accordingly redesigned. Moreover, arranging the outlet of the silicon chip, i.e. the micropump 21, together with a nozzle directly bonded to the silicon chip, directly in front of the nare allows to dose every pump stroke without any dead volume. However, it is to be noted that it is possible that the breath of the animal can contaminate the micropump 21, e.g. necessitating corresponding protection measures.

Figure 3:
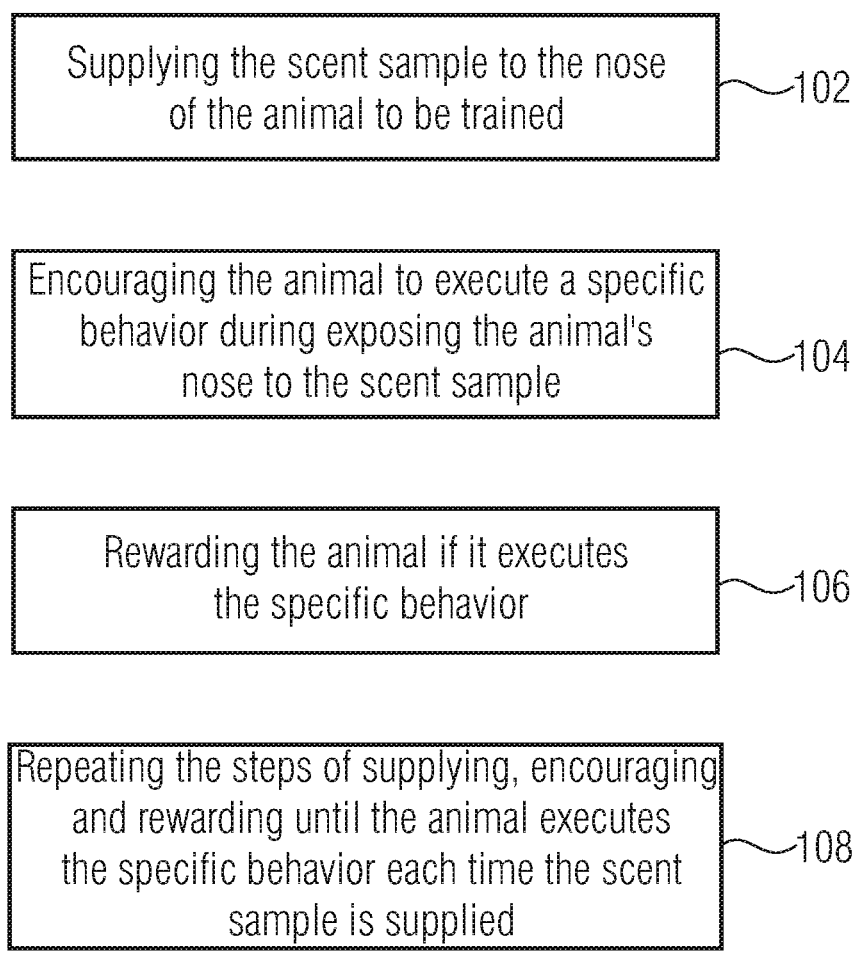
FIG. 3 shows a flowchart of a method of positive-reinforced scent training an animal for reliable recognition of a scent.

In the following, the method 100 of positive-reinforced scent training an animal for reliable recognition of a scent sample shall now be described below with reference to FIG. 3.

A possible training procedure can be executed as follows. When the scent sample is supplied 102 to the nare of the animal to be trained, the animal is encouraged 104 to execute a specific behavior during exposing the animal's nare to the scent sample. To be more specific, the animal may be instructed with a voice command or a gesture command of the animal trainer to execute the specific behavior, for example to sit, to lay down or to bark. If the animal executes this specific behavior, it is rewarded 106. Then, the steps of supplying, encouraging and rewarding are repeated 108, until the animal executes the specific behavior essentially each time the scent sample is supplied. During repeating the step of supplying, encouraging and rewarding, the encouraging of the animal can be reduced or omitted, that means for example, the encouraging of the animal can be continuously adapted based on the achieved success and/or the trainer's experience.

After having completed the training, the animal will automatically sit, lay down or bark, when it is coming in an environment containing the trained scent sample. Then, the animal handler knows that the scent sample or a real item having the specific scent is present next to the animal showing or executing the specific behavior trained.

The inventive training procedure is especially advantageous due to the following reasons. As the training procedure can be performed very efficient, training times for achieving the desired results with the animals are shorter. Moreover, the scent dosing is controllable, wherein undesirable elements of the scent signature may be eliminated. Finally, a higher detection rate of the trained animal is reached in practice, and the work for the handler can be performed on a safer basis.

Figure 4A:
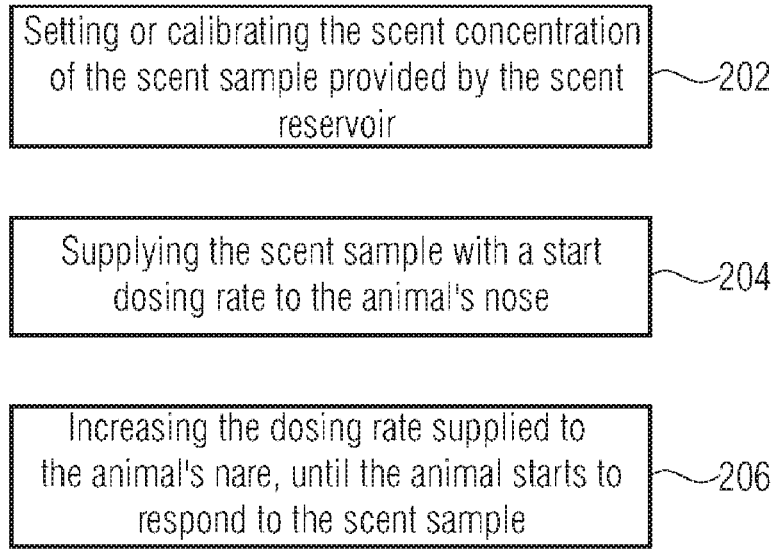
FIG. 4a-b shows flowcharts of methods for determining the minimum scent concentration of a scent sample, an animal can detect.

A method 200 for determining the minimum scent concentration of a scent sample an animal can detect in accordance with the present invention shall now be described below with reference to FIG. 4a.

To be more specific, the inventive remote controllable scent sample dispenser 10 can also be used to measure the lowest detection concentration of a scent sample, for example in a scale of parts per billion (ppb), parts per million (ppm), or parts per thousand (ppt), that an animal can detect. In this connection, it is pointed out to the fact that a detection concentration of 1 ppb means that an animal can detect one scent molecule in one billion air molecules.

For example, a regular trained and certified animal, e.g. dog, can be tested with the inventive scent sample dispenser by releasing/supplying the scent sample to the animal's nare by using the remote system controller of the trainer. First, the scent concentration of the scent sample in the scent reservoir is adjusted or calibrated 202. Then, the scent sample is supplied 204 to the animal's nare with a start dosing rate, for example 1 ppm, 1 ppb or 1 ppt. The start dosing rate is, for example, lower than the minimum dosing rate (minimum scent sample dose) the animal to be trained or tested can usually detect. The dosing rate supplied to the animal's nare is (e.g. continuously or stepwise) increased 206, until the animal responds to the scent sample. Thus, the minimum scent concentration detectable by the animal corresponds to the currently supplied dosing rate, when the animal starts to respond to the supplied scent sample. Thus, the lowest dosing rate will be the minimum detection concentration of the scent the animal can detect.

If the animal (scent detection means) already responds to the scent sample supplied with the start dosing rate, the first dosing rate is reduced by at least 50% (or 90%) to a new start dosing rate, and the steps of supplying and increasing is performed by starting with the new start dosing rate.

Figure 4B:
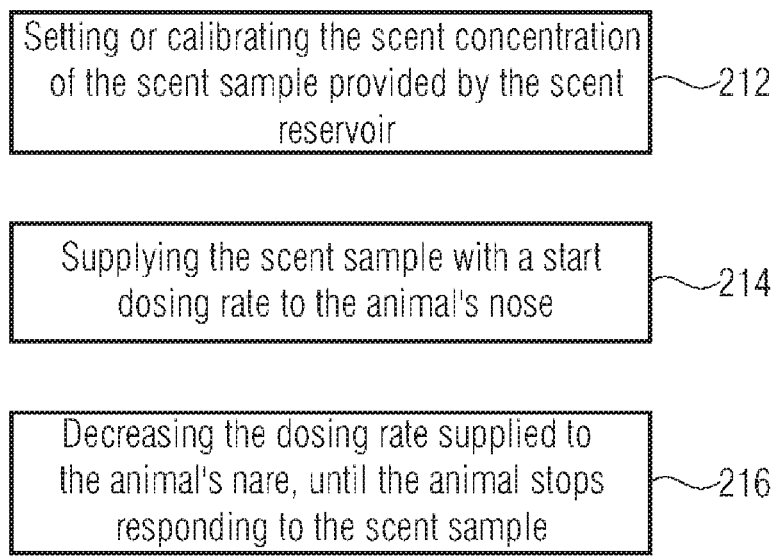

A method 210 for determining (a scent concentration of) a scent sample detection limit of an animal in accordance with the present invention shall now be described below with reference to FIG. 4b. To be more specific, the inventive remote controllable scent sample dispenser 10 can also be used to measure the lowest detection concentration of a scent sample, for example in a scale of parts per billion (ppb), parts per million (ppm), or parts per thousand (ppt), that an animal can detect.

For example, a regular trained and certified animal, e.g. a dog, can be tested with the inventive scent sample dispenser by releasing/supplying the scent sample to the animal's nare by using the remote system controller of the trainer. First, the scent concentration of the scent sample in the scent reservoir is adjusted or calibrated 212. Then, the scent sample is supplied 214 to the animal's nare with a start dosing rate, for example 1 ppm, 1 ppb or 1 ppt. The start dosing rate is, for example, higher than the minimum dosing rate (minimum scent sample dose) the animal to be trained or tested can usually detect. The dosing rate supplied to the animal's nare is (e.g. continuously or stepwise) decreased 216, until the animal stops to respond to the scent sample, i.e. the animal does not respond to the scent sample any more. Thus, the scent sample detection limit of the animal or the minimum scent sample concentration detectable by the animal corresponds to the currently supplied dosing rate, when the animal stops to respond to the supplied scent sample.

If the animal does not respond to the scent sample supplied with the start dosing rate, the first dosing rate is increased by at least 50% (or 100%) to a new start dosing rate, and the steps of supplying and decreasing is performed by starting with the new start dosing rate.

Alternatively, the inventive scent sample dispenser can be used for lung cancer research institutes and hospital oncology. For example, the patient blows in a carbon container, wherein this sample is sent to a detection center. An animal, which is trained to detect small pre-cancer cells, can be supplied with a scent sample containing the patients breath, wherein the pre-cancer cells can be regarded as the scent sample constituents, an animal can be trained for to detect.

In this connection, it is pointed to the fact the inventive remote controllable scent sample dispenser 10 can also be used to measure the lowest detection concentration of a scent sample, for example in a scale of parts per billion (ppb), parts per million (ppm), or parts per thousand (ppt), that a scent detection means can detect.

A method 300 for determining the minimum scent concentration of a scent sample, a scent detection means can detect, in accordance with the present invention shall now be described below with reference to FIG. 5a.

Figure 5A:
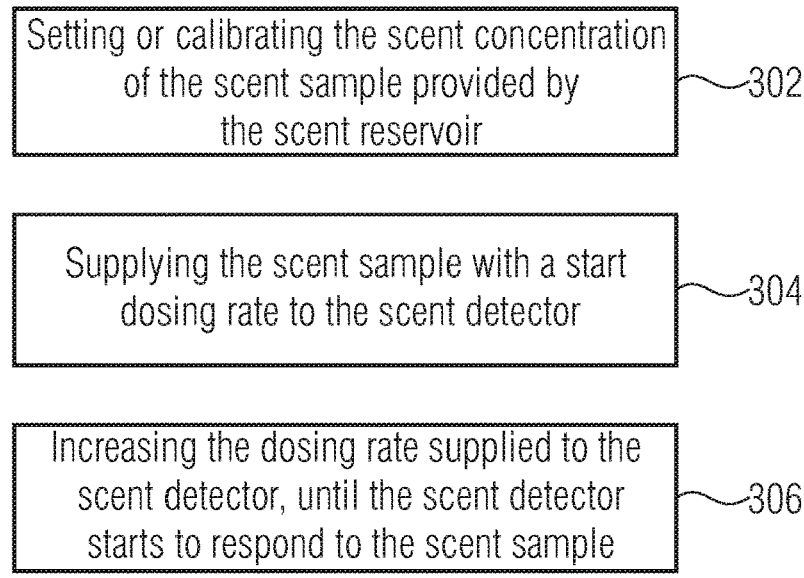
FIG. 5a-b shows flowcharts of methods for determining the minimum scent concentration of a scent sample, a scent sensor can detect.

In general, the inventive remote controllable scent sample dispenser 10 can be advantageously used for determining 300 the minimum scent concentration of a scent sample, an scent detection means can detect as shown in FIG. 5a. Thus, minute concentrations of scent samples can be supplied with a very high reliability in immediate proximity to a scent sensing element (sensor) of the scent detection means. To be more specific, the scent concentration of the scent sample provided by the scent reservoir, is adjusted or calibrated 302. The start dosing rate is, for example, lower than the minimum dosing rate (scent sample dose) the scent detection means to be tested can usually detect. Than, the scent sample is supplied 304 with the start dosing rate to a sensing element of the scent detection means, wherein the dosing rate supplied to the sensing element is (e.g. continuously or stepwise) increased 306, until the scent detection means responds to the scent sample. The minimum scent concentration detectable by the scent detection means corresponds to the currently supplied dosing rate, when the scent detection means responds to the supplied scent sample.

If the scent detection means already responds to the scent sample supplied with the start dosing rate, the first dosing rate by at least 50% (or 100%) is reduced to a new start dosing rate, and the steps of supplying and increasing is performed by starting with the new start dosing rate.

A method 310 for determining (a scent concentration of) the scent sample detection limit of a scent detection means in accordance with the present invention shall now be described below with reference to FIG. 5b.

Figure 5B:
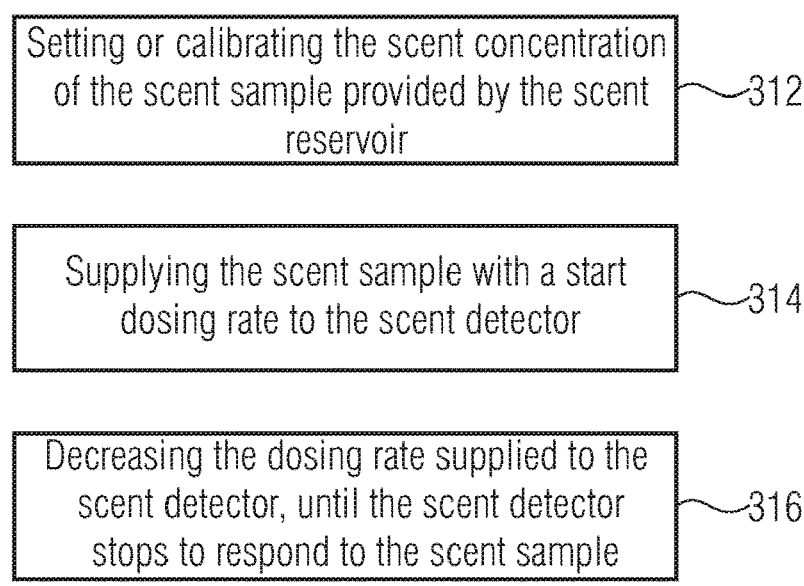

In general, the inventive remote controllable scent sample dispenser 10 can be advantageously used for determining 310 the scent sample detection limit of a scent detection means as shown in FIG. 5b. Thus, precisely dosed concentrations of scent samples can be supplied with a very high reliability in immediate proximity to a scent sensing element (sensor) of the scent detection means. To be more specific, the scent concentration of the scent sample provided by the scent reservoir, is adjusted or calibrated 312. The start dosing rate is, for example, higher than the minimum dosing rate (minimum scent sample dose) the scent detection means to be tested can usually detect. Than, the scent sample is supplied 314 with the start dosing rate to a sensing element of the scent detection means, wherein the dosing rate supplied to the sensing element is (e.g. continuously or stepwise) decreased 316, until the scent detection means stops to respond or detect to the scent sample, i.e. the scent detection means does not respond to the scent sample any more. Thus, the scent sample detection limit of the scent detection means or the minimum scent sample concentration detectable by the scent detection means corresponds to the currently supplied dosing rate, when the scent detection means stops to respond to or to detect the supplied scent sample.

If the scent detection means does not respond to the scent sample supplied with the start dosing rate, the first dosing rate by at least 50% (or 100%) is increased to a new start dosing rate, and the steps of supplying and decreasing is performed by starting with the new start dosing rate.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Depending on certain implementation requirements, embodiments of the invention can be implemented in hardware or in software. The implementation can be performed using a digital storage medium, for example a floppy disk, a DVD, a Blue-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Generally, embodiments of the present invention can be implemented as a computer program product with a program code, the program code being operative for performing one of the methods when the computer program product runs on a computer. The program code may for example be stored on a machine readable carrier.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A method of positive-reinforced scent training an animal for reliable recognition of a scent sample, comprising:
   supplying the scent sample to the nose of the animal to be trained,
   encouraging the animal to execute a specific behavior during supplying of the scent sample to the nose of the animal to be trained for exposing the animal's nose to the scent sample,
   rewarding the animal if it executes the specific behavior, and
   repeating supplying, encouraging and rewarding until the animal executes the specific behavior each time the scent sample is supplied, wherein
   the scent sample to the nose of the animal to be trained is supplied by a controllable fluid sample dispenser,
   the controllable fluid sample dispenser includes a microdosing device that outputs, during an activation state, the scent sample at a scent sample outlet to the environment,
   the microdosing device is placed adjacent to the animal's nose so that a distance between the outlet of the microdosing device and a nare or nostril of the animal's nose is within a predefined range,
   the controllable fluid sample dispenser includes a microdosing driver unit that adjusts a dosing rate of the scent sample output at the scent sample outlet by selectively activating the microdosing device,
   the microdosing device includes a micro pump having a micro-membrane or micro-diaphragm pump with a pump chamber providing a stroke volume, and
   the microdosing driver unit adjusts the dosing rate of the scent sample output at the scent sample outlet based on the stroke volume of the micro pump and a number of pump strokes or diaphragm excursions for transporting a carrier gas in a predetermined direction to the scent sample outlet.

2. The method according to claim 1, wherein encouraging comprises instructing the animal to be trained with a voice or gesture command of a trainer.

3. The method according to claim 1, wherein, during repeating supplying, encouraging and rewarding, the encouraging is reduced or omitted.

4. The method according to claim 1, wherein the controllable fluid sample dispenser comprises a further micro pump, the method further comprising:
   randomly activating the further micro pump during time periods, when the micro pump is not activated.

5. The method according to claim 4, wherein:
   the micro pump and the further micro pump are identically designed, and
   the further micro pump provides a dummy pump function without releasing any scent sample.

* * * * *